United States Patent
Ni et al.

(10) Patent No.: US 8,741,262 B2
(45) Date of Patent: Jun. 3, 2014

(54) TARGETED RADIOTHERAPY

(75) Inventors: Yicheng Ni, Herent (BE); Marie Van De Putte, Willebringen (BE); Peter DeWitte, Kessel-Lo (BE); Alfons Verbruggen, Wilsele (BE); Guy Marchal, Blanden (BE); Ziping Sun, Jinan (CN)

(73) Assignee: Katholieke Universiteit Leuven, K.U. Leuven R&D, Leuven (BE)

( * ) Notice: Subject to any disclaimer, the term of this patent is extended or adjusted under 35 U.S.C. 154(b) by 688 days.

(21) Appl. No.: 12/744,798

(22) PCT Filed: Nov. 26, 2008

(86) PCT No.: PCT/BE2008/000099
§ 371 (c)(1),
(2), (4) Date: Oct. 29, 2010

(87) PCT Pub. No.: WO2009/067767
PCT Pub. Date: Jun. 4, 2009

(65) Prior Publication Data
US 2011/0038795 A1  Feb. 17, 2011

(30) Foreign Application Priority Data
Nov. 26, 2007  (GB) .................................. 0723124.4

(51) Int. Cl.
*A61K 51/00* (2006.01)
*A61K 49/04* (2006.01)

(52) U.S. Cl.
USPC ......... 424/1.85; 424/1.11; 424/1.65; 424/9.3; 424/9.41

(58) Field of Classification Search
USPC ........... 424/1.11, 9.3, 9.6, 9.41, 144.1, 145.1, 424/649; 514/27, 263.32, 460, 381, 283, 514/254, 511, 288
See application file for complete search history.

(56) References Cited

U.S. PATENT DOCUMENTS

| | | | |
|---|---|---|---|
| 2005/0013778 A1 * | 1/2005 | Green et al. | 424/9.6 |
| 2006/0264384 A1 * | 11/2006 | Johansen et al. | 514/27 |
| 2007/0122340 A1 | 5/2007 | Yicheng et al. | |
| 2009/0274622 A1 | 11/2009 | Yicheng et al. | |

FOREIGN PATENT DOCUMENTS

| | | |
|---|---|---|
| JP | 2002-538201 A | 11/2002 |
| JP | 2011-504511 A | 2/2011 |
| WO | WO 95/31219 | 11/1995 |
| WO | WO 99/43317 | 9/1999 |
| WO | WO-99/43317 A1 | 9/1999 |
| WO | WO 2005/009423 * | 2/2005 |
| WO | WO 2005/009423 A1 | 2/2005 |
| WO | WO-2006/002122 A2 | 1/2006 |
| WO | WO-2007/002500 A1 | 1/2007 |
| WO | WO 2009/067767 A2 | 6/2009 |

OTHER PUBLICATIONS

Dietmar W. Siemann et al., Vascular-Targeting Therapies for Treatment of Malignant Disease, Cancer, vol. 100(12), 2491-2499.*
Guy Bormans et al., Preparation, analysis and biodistribution in mice of iodine-123 labelled derivatives of hypericin, J Label compd Radiopharm 2004; 47; 191-198.*
Masato Kato et al., Distinct Structural Mechanisms for Inbibition of Pyruvate Dehydrogenase Kinase Isoforms by AZD7545, Dichloroacetate, and Radicicol, Structure 15, 992-1004, 2007.*
Dietmar W. Siemann et al., Vascular-Targeting Therapies for Treatment of Malignant Disease, Cancer, 2004, vol. 100(12), 2491-2499.*
Bhuvaneswari et al., "Hypericin-mediated photodynamic therapy in combination with Avastin (bevacizumab) improves tumor response by downregulating angiogenic proteins," *Photochemical & Photobiological Sciences* 6:1275-1283, 2007.
Bormans et al., "Preparation, analysis and biodistribution in mice of iodine-123 labelled derivatives of hypericin," *J Label Compd Radiopharm* 47:191-198, 2004.
Chen et al., "Potentiation of Photodynamic Therapy with Hypericin by Mitomycin C in the Radiation-induced Fibrosarcoma-1 Mouse Tumor Model," *Photochemistry and Photobiology* 78(3):278-282, 2003.
Van de Putte et al., "Elucidation of the tumoritropic principle of hypericin," *British Journal of Cancer* 92:1406-1413, 2005.
International Search Report for International Application No. PCT/BE2008/000099, mailed Dec. 3, 2009.
Written Opinion of the International Searching Authority for International Application No. PCT/BE2008/000099, mailed Dec. 3, 2009.
Search Report for UK Application No. GB0723124.4, dated Mar. 14, 2008.
Chen et al., "Potentiation of photodynamic therapy with hypericin by mitomycin C in the radiation-induced fibrosarcoma-1 mouse tumor model," Photochem Photobiol. 78(3):278-282 (2003).
Fonge et al., "Evaluation of tumor affinity of mono-[$^{123}$I]iodohypericin and mono-[$^{123}$I]iodoprotohypericin in a mouse model with a RIF-1 tumor," Contrast Media Mol Imaging 2(3):113-119 (2007).
Fonge et al., "Synthesis and preliminary evaluation of mono-[$^{123}$I]iodohypericin monocarboxylic acid as a necrosis avid imaging agent," Bioorg Med Chem Lett. 17(14):4001-4005 (2007).

(Continued)

*Primary Examiner* — Michael G Hartley
*Assistant Examiner* — Jagadishwar Samala
(74) *Attorney, Agent, or Firm* — Clark & Elbing LLP (57) ABSTRACT

The present invention concerns a therapeutically labeled napthodianthrone or phenanthro[1,10,9,8-opqra]perylene-7,14-dione compound, which comprises a chemical element or an isotope that has an unstable nucleus and emits radiation during its decay to a stable form sufficient to destroy neighboring cells or tissues for use in a targeted radiotherapy to enhance curability of a warm-blooded animal that has been subjected to a necrosis-inducing antitumor therapy. A particular advantage of present invention is that viable rim resistant to a necrosis-inducing antitumor therapy such as vascular targeting agent (VTA) can be supplemented by one single or repeated doses of a therapeutically radiolabeled small molecule necrosis-avid chemical compound treatment to enhance the curability. Examples of necrosis inducing therapies are for instance minimally invasive tumor ablations applied chemically by percutaneous injection of ethanol or acetic acid, or physically by cryotherapy, microwave, focused ultrasound, interstitial laser therapy and radio-frequency ablation (RFA); by chemotherapies using cytotoxic agents or vascular targeting agents (VTA); and by external or internal radiotherapies.

15 Claims, 3 Drawing Sheets

(56) References Cited

OTHER PUBLICATIONS

Kim et al., "Facile synthesis and radioiodine labeling of hypericin," Bull Korean Chem Soc. 25(8):1147-1150 (2004).
Fourth Office Action for Chinese Patent Application No. 200880125605.6, dated Jul. 10, 2013 (10 pages).
Notification of Reasons for Refusal for Japanese Patent Application No. 2010-535181, mailed May 21, 2013 (8 pages).
Communication under Rule 71(3) EPC issued in European Patent Application No. 08854013.3, dated Nov. 30, 2011.
Druckexemplar for European Patent Application No. 08854013.3, posted Nov. 31, 2011.
Communication Pursuant to Rules 161(1) and 162 EPC issued in European Patent Application No. 08854013.3, dated Jul. 8, 2010.
To the Communication Pursuant to Rules 161 and 162 EPC dated Jul. 8, 2010, as filed Aug. 18, 2010.
Third Office Action issued in Chinese Patent Application No. 200880125605.6, dated Nov. 5, 2012 (English Language Translation Provided) (12 pages).
International Preliminary Report on Patentability for International Patent Application No. PCT/BE2008/000099, completed and mailed Jul. 6, 2010.
English Language Translation of Office Action issued in Chinese Patent Application No. 200880125605.5, dated May 15, 2012 (6 pages).
English language translation of Office Action for Chinese Patent Application No. 200880125605.6, dispatched Nov. 9, 2011.

* cited by examiner

TARGETED RADIOTHERAPY

CROSS-REFERENCE TO RELATED APPLICATIONS

This application is the national stage of International Application No. PCT/BE2008/000099, filed Nov. 26, 2008, which claims benefit of UK Patent Application No. GB0723124.4, filed Nov. 26, 2007.

FIELD OF THE INVENTION

The present invention concerns a therapeutically labeled napthodianthrone or phenanthro[1,10,9,8-opqra]perylene-7, 14-dione compound, which comprises a chemical element or an isotope that has an unstable nucleus and emits radiation during its decay to a stable form sufficient to destroy neighboring cells or tissues for use in a targeted radiotherapy to enhance curability of a warm-blooded animal that has been subjected to a necrosis inducing antitumor therapy. A particular advantage of present invention is that viable rim or tumor residuals resistant to the necrosis inducing antitumor therapy such as vascular targeting agent (VTA) can be complementarily treated by one or more intravenous doses of therapeutically radiolabeled necrosis-avid small molecules of the group of the napthodianthrone or phenanthro[1,10,9,8-opqra]perylene-7,14-dione compounds that selectively accumulate in the prior formed intratumoral necrosis and emit radiation to neighboring viable tumor cells in order to achieve the effect of radical treatment.

BACKGROUND OF THE INVENTION

Cancer remains a most life-threatening disease worldwide. Conventional radiotherapy and chemotherapy are generally regarded palliative only to slow down tumor growth and prolong patient survival, yet at a cost of systemic adverse effects. The best curative option is radical surgery, but only a limited number of patients are suitable due to unfavorable location, staging and extent of the tumor. Furthermore, limited functional reserve of the organ after partial resection is also associated with a higher post-operative risk. Societal communities, healthcare institutions and medical professionals have put tremendous efforts in the research and development of new treatments to combat cancer. Among newly developed anticancer therapies, vascular targeting agents (VTAs) selectively disrupt the cytoskeleton of endothelial cells of neovasculature and cause shutdown of tumoral blood supply and subsequent tumor cell starvation and death [Thorpe P E. Clin Cancer Res. 2004; 10: 415-27]; radiofrequency ablation (RFA) is a minimally invasive procedure that utilizes heat converted from RF energy to destroy biological tissues particularly for the treatment of solitary tumors [Ni Y, et al; Abdominal Imaging 2005; 30: 381-400]; photodynamic therapy (PDT) combines administration of a drug or photosensitizer with light illumination of certain wavelength to kill cancer cells by the generated cytotoxic species [Pass H, J Natl Cancer Inst 1993; 85: 443-56]. A common noticeable consequence of these therapies is creation of tumor necrosis. On the other hand, the use of pyruvate dehydrogenase kinase inhibitors such AZD7545, dichloroacetate (DCA), sodium dichloroacetate, trichloroacetate, difluoroacetate, 2-chloropropionate, 2,2'-dichloropropionate, chloropropionate, halogenated acetophenones inhibitors, radicicol oxime or radicicol that that blocks mitochondrial pyruvate dehydrogenase kinase (PDK) shifting metabolism from glycolysis to glucose oxidation promoting apoptosis in cancer tumors [Alla Klyuyeva et al. FEBS Lett. 2007 June 26; 581(16): 2988-2992 and Biochem. J. 329 191. Bonnet et al (2007)*.

Despite encouraging preclinical and clinical outcomes with RFA, VTAs and PDT as well as other conventional nonsurgical anticancer treatments to induce therapeutic tumor necrosis, marginal or sporadic tumor residues are frequently attributed to the eventual incomplete treatment and tumor relapse [Ni Y, Miao Y, et al. Eur Radiol 2000; 10: 852-4 and Thoeny H C, et al. Radiology 2005; 237:492-9.].

Present invention demonstrates that small therapeutically labeled necrosis-avid compounds (SRaLNACs, MW<1-2 K Dalton) such as the therapeutically labeled napthodianthrone or phenanthro[1,10,9,8-opqra]perylene-7,14-dione compound with a high in vivo target-to-nontarget ratio of, for instance, 10-100 (in contrast to other compounds with a poor target-to-nontarget ratio of, for instance, close to 1.0) can be applied in combination with any necrosis-inducing anticancer therapies to prevent the formation of rims or clusters of viable tumor cells, and thus synergistically augment tumoricidal efficacy and cancer curability.

The therapeutically labeled napthodianthrone or phenanthro[1,10,9,8-opqra]perylene-7,14-dione compound can be used to block the proliferation reaction of viable tumor cells as a response to tumor damage, tumor ablation or tumor destruction, to block tumor cell proliferation as response to an incomplete antitumor treatment, to prevent repopulation of tumor cells in solid tumors after physically or chemically induced tumor destruction, to prevent re-growth of tumors after chemotherapy induced tumor shrinkage, or to remove the remaining antitumor-drug resistance cancer cells in the primary or metastatic solid tumors or in the locoregional tissues adjacent to such tumors. Suitable therapeutic labels for napthodianthrone or phenanthro[1,10,9,8-opqra]perylene-7,14-dione compound to obtain such radio-emitters are from the group consisting of $^{153}$Samarium, $^{156}$Holmium, $^{165}$Dysprosium, $^{203}$Lead, $^{186}$Rhenium, $^{88}$Rhenium, $^{211}$Bismuth $^{212}$Bismuth, $^{213}$Bismuth, and $^{214}$Bismuth, $^{153}$Sm, $^{159}$Gd, $^{186}$Re, $^{166}$Ho, $^{90}$Yttrium, $^{91}$Yttrium, $^{88}$Yttrium, $^{89}$Yttrium and $^{131}$Iodine.

SUMMARY OF THE INVENTION

The present invention is directed, in part, to radiopharmaceutical compositions for use in a medicament to improve the efficacy and effectiveness of tumoricidal treatments of primary or metastatic solid tumors by chemotherapy (for instance therapy by vascular targeting agents or VTAs) or by physically or chemically induced ablation (for instance by radiofrequency ablation or RFA) or any other existing effective nonsurgical anticancer therapies. More particularly the present invention is directed to therapeutically radionuclide-labeled napthodianthrone or phenanthro[1,10,9,8-opqra]perylene-7,14-dione compound to form a necrosis-avid chemical compounds for use in a medicament to block tumor cell proliferation as response to an incomplete antitumor treatment, or to prevent repopulation of tumor cells in solid tumors after physically or chemically induced tumor destruction, or to prevent re-growth of tumors after chemotherapy induced tumor shrinkage, or to remove the remaining antitumor-drug resistance cancer cells in the primary or metastatic solid tumors or in the locoregional tissues adjacent to such tumors.

The term "small molecule(s)", as used herein, refers to organic molecules having a molecular weight less than 5000 dalton, preferably less than 2000 dalton and most preferably less than 1000 dalton, other than the immune glycoproteins or protein fragments thereof. Such chemical compounds can be either synthesized or found in nature. Such small molecules for the present invention may be conjugated with therapeutic radioactive isotopes and/or diagnostic markers (for instance paramagnetic elements).

The term "tumoricidal compound(s)" is in the meaning of compounds that are destructive to tumor cells. Such compounds may be enterotoxins or homologous compounds known as superantigens. They are in particular tumoricidal when they are expressed on the surface of lipid droplets (in adjuvant-vehicle formulations) or expressed on biologic cell surfaces as a result of enterotoxin gene-transfection and used to produce a tumoricidal response in a tumor bearing host. Tumoricidal effects of superantigens were demonstrated in four of five patients with advanced breast cancer utilizing therapy with plasma perfused over Staphylococcal Protein A. (Terman, D. S., Young, J. B., Shearer, W. T., Ayus, C., Lehane, D., Mattioli, C., Espada, R., Howell, J. F., Yamamoto, T., Zaleski, H. E., Miller, L., Frommer, P., Feldman, L., Henry, J. F., Tiliquist, R., Cook, G., Daskal, Y., New Eng. J. Med., 305, 1195, 1981). This elaborate system involved the administration of patient plasma which was perfused over a solid surface to which Staphylococcal Protein A was chemically attached. Protein A was prepared by batch fermentation of Staphylococcus. It was isolated from the media and partially purified by affinity chromatography. U.S. Pat. No. 6,692,746 describes tumor killing effects of enterotoxins, superantigens, and related compounds A "chemotherapeutic agent" is a chemical compound useful in the treatment of cancer. Examples of chemotherapeutic agents include alkylating agents such as thiotepa and cyclosphosphamide (CYTOXAN®.); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, caliceamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazine; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®., Bristol-Myers Squibb Oncology, Princeton, N.J.) and docetaxel (TAXOTERE®., Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, dichloroacetate (DCA) and goserelin; and pharmaceutically acceptable salts, acids or derivatives of any of the above.

The term "warm-blooded animal" for the present invention also comprises the meaning of a human.

The term "Antitumor agent(s)" as used herein concerns agents, compounds (e.g. chemotherapy by cytotoxic compounds) or physical agents (e.g. radiofrequency ablation), that destruct or shrink tumors or inhibit their growth. For instance U.S. Pat. No. 6,506,739 B1 describes chemical antitumor agents of the groups of Bis-(N,N'-bis-(2-haloethyl)amino)phosphoramidates, while U.S. Pat. No. 6,514,251 B "Cooled-wet electrode" describes physical antitumor therapy by delivering radiofrequency (RF) energy to induce tumor ablation procedures.

Antitumor chemotherapy can be efficient for tumors with high growth fractions, such as acute myelogenous leukemia and the aggressive lymphomas, including Hodgkin's disease which are most sensitive to chemotherapy, as a larger proportion of the targeted cells are undergoing cell division at any time. However, malignancies with slower growth rates, such as indolent lymphomas, tend to respond to chemotherapy much more modestly. Drugs affect "younger" tumors more effectively, because mechanisms regulating cell growth are usually still preserved. With succeeding generations of tumor cells, differentiation is typically lost, growth becomes less regulated, and tumors become less responsive to most chemotherapeutic agents. Near the center of some solid tumors, cell division has effectively ceased, making them insensitive to chemotherapy. Another problem with solid tumors is the fact that the chemotherapeutic agent often does not reach the core of the tumor. There is therefore an urgent need in the art for an effective therapy in which the central chemoinsensitive tumor cells are destructed.

Over time, cancer cells become more resistant to chemotherapy treatments. A possible solution is the combination of various therapeutics for instance of the conventional cytotoxics with other chemotherapeutics such as, vascular damaging agents or anti-angiogenic drugs. Despite the effectiveness when used in combination, the chemotherapies must be administered in repeat daily doses following initial VTA administration or anti-angiogenic administration in order to achieve prolonged tumor regression. Most chemotherapeutics therapies are highly cytotoxic, and the most patients cope with prolonged side effects (emesis, hair loss, myelosuppression, etc.) due to chronic administration. There is therefore an urgent need in the art for an effective therapy in which the repeated chemotherapy can be reduced.

The term "Vascular Targeting Agent(s)" ("VTA(s)"), also known as Vascular Damaging or Disrupting Agents (VDAs), are a novel class of antineoplastic drugs which attack solid tumors by selectively targeting and destroying the existing neovasculature or vasculature newly formed by angiogenesis. The cytotoxic mechanism of VTA action is quite divorced from that of anti-angiogenic agents. A single dose of VTA can cause a rapid and selective shutdown of the tumor neovasculature within a period of minutes to hours, leading eventually to tumor necrosis by induction of hypoxia and nutrient depletion. The most described VTA is CA4DP, a disodium salt of the phosphate prodrug of CA-4. The invention is not limited in this respect, however, and other phosphate prodrug salts of CA-4 such as those disclosed in WO 02/22626 and WO 99/35150 may work as well or better than CA4DP. But also other combretastatins that have been isolated, structurally elucidated, and synthesized. U.S. Pat. Nos. 5,409,953, 5,569,786, and 4,490,726 describe the isolation and synthesis of Combretastatins designated as A-1, A-2, A-3, B-1, B-2, B-3, B-4, D-1, and D-2. Some of these compounds have been modified as phosphate prodrugs as disclosed in WO 01/81355 or the synthetic analogs of the Combretastatins as described in Bioorg. Med. Chem. Lett. 11(2001) 871-874, 30733076, J. Med. Chem. (2002), 45:1697-1711, WO 01/12579, WO 00/35865, WO 00/48590, WO 01/12579, U.S. Pat. No. 5,430,062, U.S. Pat. No. 5,525,632, U.S. Pat. No. 5,674,906, and U.S. Pat. No. 5,731,353, the entire disclosures of which are incorporated herein by reference. Yet other tubulin binding agents which may be administered as VTAs include the following agents or their prodrugs: 2,3-disubstituted Benzo[b]thiophenes (U.S. Pat. Nos. 5,886,025; 6,162,930, and 6,350,777), 2,3-disubstituted benzo[b]furans (WO 98/39323), 2-3-disubstituted indoles (WO 01/19794), disubstituted dihydronaphthalenes (WO01/68654), Colchicine analogs (WO 99/02166, WO 00/40529, WO 02/04434, WO 02/08213), Chalcone analogs (WO 02/47604) the entire disclosures are incorporated by reference herein. Finally, additional non-cytotoxic prodrugs of tubulin binding agents, which are converted to a substantially cytotoxic drug by action of an endothelial enzyme are disclosed in WO 00/48606, which is incorporated by reference here. The anti-tumor effect may be attributed to the initial blood flow shutdown and subsequent necrosis. Other agents have been known to disrupt tumor vasculature but differ in that they also manifest substantial normal tissue toxicity at their maximum tolerated dose. In contrast, genuine VTAs, such as the combretastatins, retain their vascular shutdown activity at a fraction of their maximum tolerated dose. Combretastatin A-4 Disodium Phosphate Prodrug ("CA4DP") is the lead drug of a group of VTAs currently in clinical trials as a VTA. This compound was initially isolated as Combretastatin A-4 ("CA-4") from the stem wood of the African tree Combretum caffrum (Combretaceae). As described in U.S. Pat. No. 4,996,237, the entire disclosure of which is incorporated herein in entirety, CA-4 was synthesized and found to have tubulin binding activity. Moreover, CA4DP was found to be a potent inhibitor of microtubule assembly in tumor endothelium. However, due to the insolubility of CA-4 in human plasma, CA4DP was developed and found to have superior activity as a VTA (U.S. Pat. No. 5,561,122, the entire disclosure of which is incorporated by reference). When administered to the bloodstream of a patient, the CA4DP is cleaved to the active, tubulin-binding CA-4 by endogenous nonspecific phosphatases. It is thought that CA-4 selectively destabilizes the microtubule cytoskeleton of tumor endothelial cells, causing a profound alteration in the shape of the cell which ultimately leads to occlusion of the tumor blood vessel and shutdown of blood flow to the tumor (Kanthou and Tozer, Blood, 2002, 99(6): 2060-2069). ZD6126 or N-acetylcolchinol is a water-soluble phosphate prodrug of the tubulin-binding agent with similar antitumor effects (Davis P D et al, Cancer Research 2002; 62:7247-53). While in vivo studies have confirmed that vascular damaging effects of VTAs on tumor tissue far exceed the effects on normal tissues, only in a few cases has a tumor regression or complete tumor response been observed when these agents are used alone as a monotherapy. Such incomplete tumor response has been attributed to the rapid in situ recolonization of a viable rim of well-oxygenated tumor cells that have survived the effects of vascular targeting agents (Chaplin, et al., Anticancer Research, 1999, 19(1A):189-195).

Examples of necrosis-inducing therapies include, for instance, minimally invasive tumor ablations applied chemically by percutaneous ethanol or acetic acid injection, or physically by cryotherapy, microwave, focused ultrasound, interstitial laser therapy and radiofrequency ablation (RFA); chemotherapies using cytotoxic agents or vascular targeting agents (VTAs); and radiotherapies by external or internal eradiation of tumor tissues.

The term for "necrosis-avid" for present invention is used for compounds that selectively accumulate in nonviable tissues, in particular, in necrotic tissue. Necrosis-avidity appears a natural process in the living being that involves a great diversity of endogenous and exogenous chemicals. For the present invention such necrosis-avid small molecules are non immune-originated and are labeled with a therapeutic moiety such as a radionuclide and are hereby called "therapeutically labeled necrosis-avid small molecules" for instance a small molecule that possesses necrosis avidity and has been labeled by a therapeutical radio-isotope or radio-element. Phenanthro[1,10,9,8-opqra]perylene-7,14-dione or hypericin or its derivatives is found necrosis avid. Hypericin is a substance isolated from a medicinal herb Hypericum perforatum, commonly known as St. John's Wort. Hypericin belongs to group of compound known as napthodianthrones (Southwell I A & Campbell M H: Hypericin content variation in Hypericum perforatum in Australia. Phytochemistry 1991; 30:475-478 and Kitanov, G. M., 2001. Hypericin and pseudohypericine in some Hypericum species. Biochemical Systematics and Ecology 29, pp. 171-178)

"Locoregional" means limited to a local region and "Local" for the present invention refers to the therapeutic effect to be formed by therapeutically labeled necrosis-avid small molecules at or near the location of such therapeutically labeled necrosis-avid small molecules or the direct environment thereof for instance a zone of radiation by its radiolabel. Such zone is radiated in a precision manner by the radio-elements or the radioisotopes of the therapeutically labeled necrosis-avid small molecules creating a zone of cell destruction neighbouring the therapeutically labeled necrosis-avid small molecules.

Tumor relapse is a well known phenomenon of tumor re-growth or even enhanced tumor re-growth post-treatment. A primary tumor may give seed to a primary tumor relapse. Tumor relapse can result from a proliferation reaction of viable tumor cells as a response to tumor damage, tumor ablation or tumor destruction, or as response to an incomplete antitumor treatment. Some mechanism have been suggested to be involved in tumor relapse such as interferon gamma which is described as a signaling proteins involved in tumor relapse (Kmieciak, M et al EUROPEAN JOURNAL OF IMMUNOLOGY, 37 (3): 675-685 March 2007).

A nuclear therapeutical label can be a radiolabel or radionuclide that provides sufficient radiation to destroy cells in its direct environment.

The preferred radionuclide complex for the present invention is a complex that emits a beta energy of >0.5 MeV, more preferably >1 MeV and has a radionuclide half-life of days to weeks, most preferably 3-8 days.

The preferred radionuclide complex for the present invention is a complex that emits a beta energy of >0.5 MeV, more preferably >1 MeV and has a radionuclide half-life of less than 10 days, most preferably 3-8 days.

Figure 1:
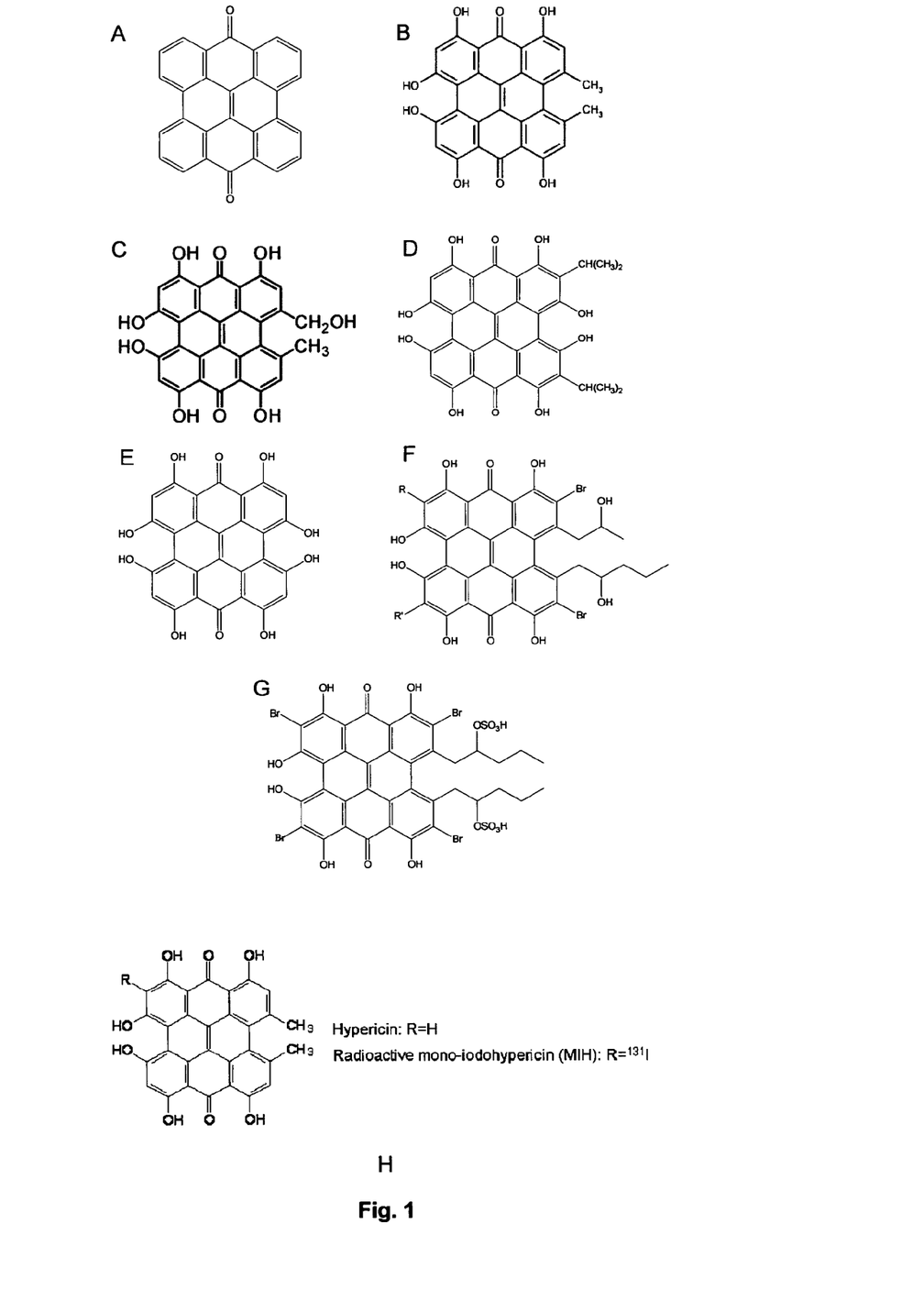
FIG. 1 displays the structures of The phenanthro[1,10,9,8-opqra]perylene-7,14-dione derivatives, for instance hypericin or its derivatives, the a napthodianthrone-type molecules are also useful NACC small molecules for the present invention Particular useful compounds for the use in present invention are therapeutically labeled. phenanthro[1,10,9,8-opqra]
Figure 2:
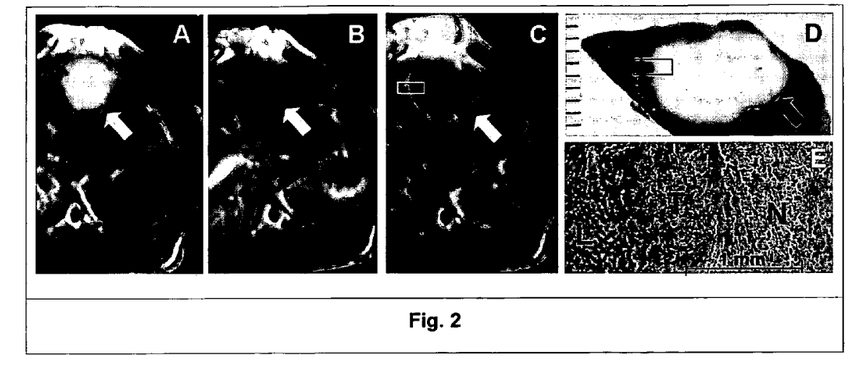
Figure 3:
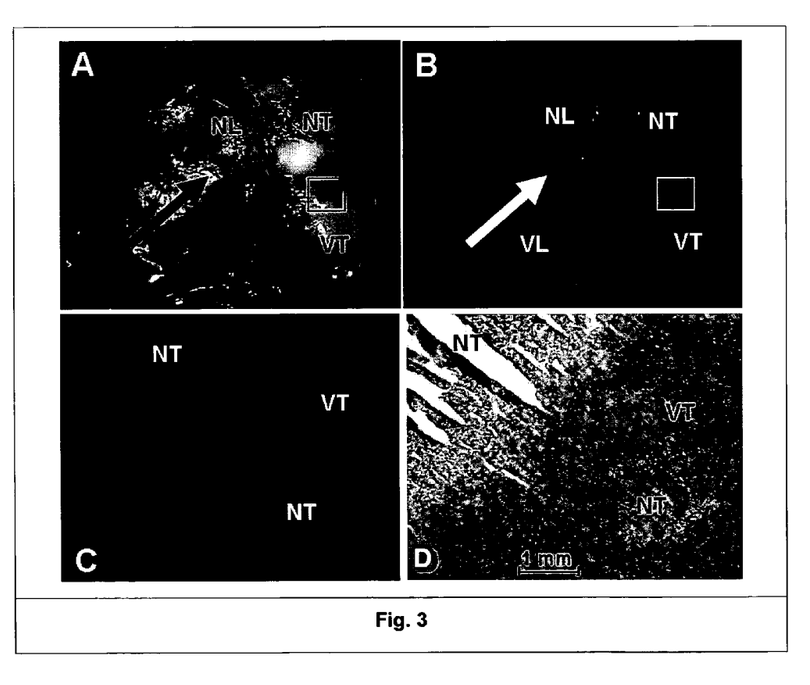
Figure 4:
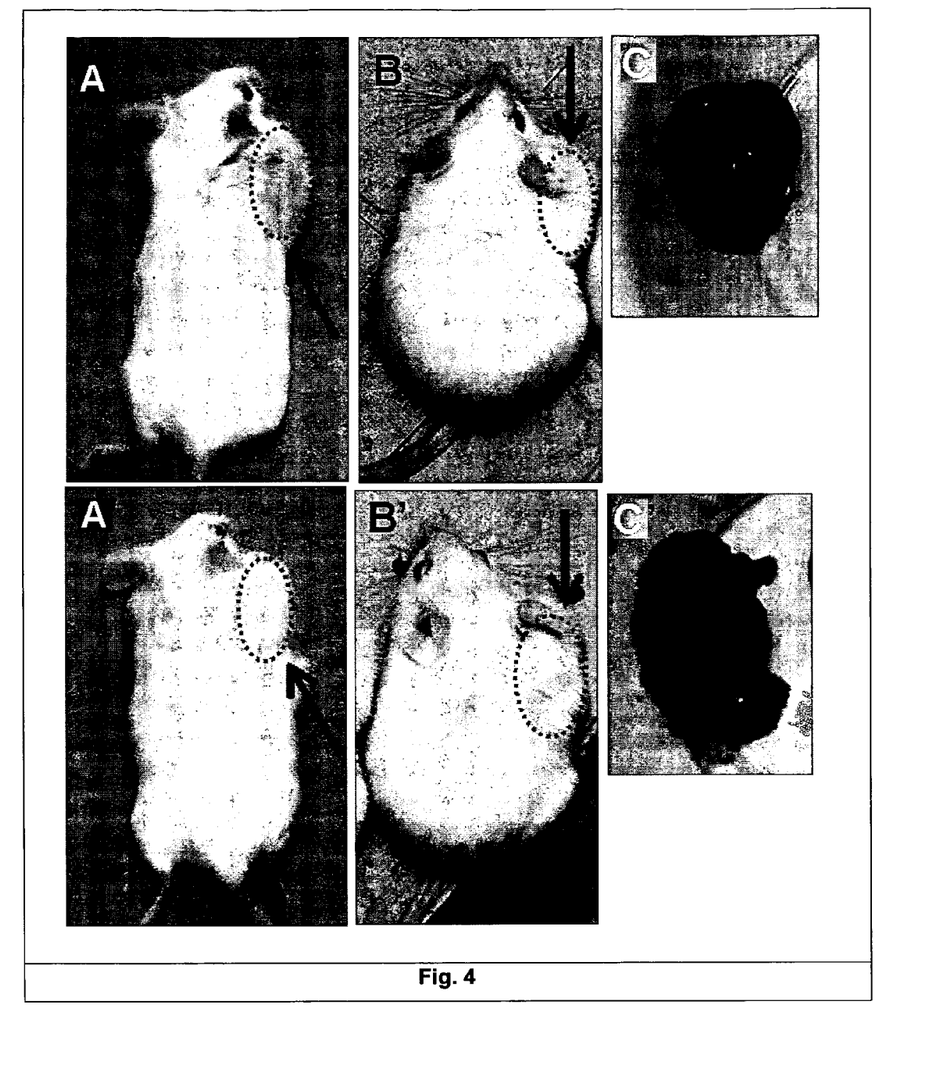
FIG. 4 demonstrates preliminary results in mouse H22 tumor shoulder implantation models treated with targeted radiotherapy of iodine-131-Hypericin following a vascular targeting agent 24 h in advance (A-C) in comparison with a control mouse (A'-C').

The phenanthro[1,10,9,8-opqra]perylene-7,14-dione derivatives, for instance hypericin or its derivatives, the a napthodianthrone-type molecules (FIG. 1A), are also useful necrosis avid chemical compound (NACC) small molecules for the present invention. Particular useful compounds for the use in the present invention are therapeutically labeled. phenanthro[1,10,9,8-opqra]perylene-7,14-diones derivatives consisting of hypericin (FIG. 1B), pseudohypericin (FIG. 1C), stentorin (FIG. 1D), the fringelites (FIG. 1E), the gymnochromes (Gymnochrome B (FIG. 1F), Gymnochrome D (FIG. 1G), Isogymnochrome D) and blepharismin (P. S. Song, 1995, J Photoscience 2, 21-35. A preferred therapeutically labeled phenanthro[1,10,9,8-opqra]perylene-7,14-dione derivatives is the compound with the structure as displayed in FIG. 1H.

As hypericin is a polyphenolic polycyclic quinone, it can be labeled efficiently and quite simply with radioiodine by electrophilic substitution in ortho position of a phenol. Structural analysis of the radioiodinated derivative has shown that in this way one iodine-131 radionuclide is reproducibly introduced on carbon atom 2, in ortho position of the phenolic group with the most acidic characteristics. The resulting mono-[$^{131}$I]iodohypericin (MIH) can efficiently be separated from the starting material hypericin by reversed phase HPLC and was obtained with an over 99% purity in non-carrier added form. HPLC purified MIH was injected in rats with partial reperfused liver infarction. Iodine-131-($^{131}$I), also called radioiodine, is a radioisotope of iodine that can be used as a radioactive label for radiopharmaceuticals. $^{131}$I decays having a half-life of 8.0197 days with beta and gamma emissions. This nuclide of iodine atom has 78 neutrons in nucleus, the stable nuclide $^{127}$I has 74 neutrons. On decaying, $^{131}$I transforms into $^{131}$Xe.

The therapeutically labeled napthodianthrone or phenanthro[1,10,9,8-opqra]perylene-7,14-dione compound can include radionuclides selected from the group consisting of 153Sm, 90Y, 159Gd, 186Re, and 166Ho (half-life 26.8 hr.) complexed with a therapeutically labeled necrosis-avid small molecules targeting complexing ligand. The preferred radioisotope is $^{90}$Yttrium ($^{90}$Y). Natural yttrium is composed of only one isotope (Y-89). The most stable radioisotopes are Y-88 which has a half life of 106.65 days and Y-91 with a half life of 58.51 days. All the other isotopes have half lives of less than a day except Y-87 which has a half life of 79.8 hours. The dominant decay mode below the stable Y-89 is electron capture and the dominant mode after it is beta emission. Twenty six unstable isotopes have been characterized.

Alternatively such therapeutically labeled necrosis-avid small molecules can be loaded either with the radioactive isotope (e.g. yttrium-90) and with the radiosensitizing metal such as gadolinium or the radiosensitizing gadolinium can be replaced by radionuclide moiety. A chelator or other binding moiety on the therapeutically labeled necrosis-avid small molecules can bind a radiolabel, e. g. yttrium-90 and/or a radiosensitizing metal ion such as gadolinium. To share the same therapeutically labeled necrosis-avid small molecules.

If the therapeutically labeled necrosis-avid small molecules comprise the radiosensitizing gadolinium and a suitable radionuclide will be used for therapeutic radiation and easy localization. The therapeutically labeled necrosis-avid small molecules will target the necrosis in the tumor and therefore will be in close proximity to each other on the tumor so that both effective radiation therapy and radiosensitization is possible. Beside gadolinium, radiosensitizing moieties which might be attached to such therapeutically labeled necrosis-avid small molecules include iodine atoms or iodine-containing moieties, e.g. triiodobenzene derivatives, or boron atoms or boron-containing moieties such as boranes or carboranes. However, any other radiosensitizing moiety known in the field might be used as well, e.g. platinum-containing moieties, imidazoles or others. Instead of coupling the radiosensitizing moiety directly to the radiolabeled drug, an analogue of the radiolabeled drug might be synthesized such that the radiolabel-containing part is exchanged for a moiety containing the radiosensitizer, i.e. an analogue of the radiolabeled drug where a radiosensitizer is in the place of the radiolabel.

If such a therapeutically labeled necrosis-avid small molecule is labeled with a radiopaque material it can be simultaneously located as a contrast agent in an X-ray procedure. Suitable radiopaque materials are well known and include iodine compounds, barium compounds, gallium compounds, thallium compounds, and the like. Specific examples of radiopaque materials include barium diatrizoate, ethiodized oil, gallium citrate, iocarmic acid, iocetamic acid, iodamide, iodipamide, iodoxamic acid, iogulamide, iohexol, iopamidol, iopanoic acid, iopromic acid, iosefamic acid, ioseric acid, iosulamide meglumine, iosumetic acid, iotasul, iotetric acid, iothalamic acid, iotroxic acid, ioxaglic acid, ioxotrizoic acid, ipodate, meglumine, metrizamide, metrizoate, propyliodone and thallous chloride.

According to the invention, beside radiotherapy, if metal complexes of therapeutically labeled necrosis-avid small molecules are also used for NMR diagnosis, the metal must be paramagnetic or super paramagnetic to be detected by or to enhance the effects of magnetic resonance imaging (MRI). This can be an element from the series of transition metals or lanthanides. Suitable ions include those of the elements copper, chromium, iron, manganese, gadolinium, and dysprosium. It is preferred that these metal atoms be prepared in the form of a conventional organometallic chelates, which are then bound to the NACC. If the metal complexes according to the invention are used for radiodiagnosis and/or radiotherapy, the metal can be radioactive. This can be an isotope from the series of elements Tc, In, Rh, Ga, Sc, Bi, Y, Fe, Sm, Ho, Co, Cu, Gd, and Eu. As suitable chelating agents, the following can be mentioned by way of example: 2-(4-Ethoxybenzyl)-3,6,9-tris(carboxymethyl)-3,6,9-triazaundecane-1,11-dicarboxylic acid (ligand of Eovist®, EP 405704; 2-(4-benzyloxybenzyl)-3,6,9-tris(carboxymethyl)-3,6,9-triazaundecane-1, 11-dicarboxylic acid, EP 405704; 2-(4-butylbenzyl)-3,6,9-tris(carboxymethyl)-3,6,9-triazaundecane-1,11-dicarboxylic acid, WO 95/28179; 2,5,8,11-tetrakis(carboxymethyl)-2,5,8,11-tetraazabicyclo[10,4,0]-hexadecane, U.S. Pat. No. 5,358,704; 2,5,12,15-tetrakis(carboxymethyl)-2,5,12,15-tetraazatricyclo[10,4,0,0$^{6,11}$]-icosane, U.S. Pat. No. 5,358,704; 10-[1-methyl-2-oxo-3-aza-5-oxo-5-{4-perfluorooctylsulfonyl-piperazin-1-yl}-pentyl]-1,4,7-tris(carboxymethyl)-1,4,7,10-tetraazacyclododecane, WO 97/26017; 10-[2-hydroxy-4-aza-5-oxo-7-oxa-10,10,11, 11,12,12,13,13,14,14,15,15,16,16,17,17,17,-heptadecafluoroheptadecyl]-1,4,7-tris(carboxymethyl)-1,4,7,10-tetraazacyclododecane, WO 97/26017; 2-[1,4,7,10-tetraaza-4,7,10-tris(carboxymethyl)cyclododecan-1-yl]-3- benzyloxypropionic acid, WO 89/05802; 2-benzyloxymethyl-3,6,9-tris(carboxymethyl)-3,6,9-triaza-undecane-1,11-dicarboxylic acid, EP 230893; DTPA-Lys-Asp-Asp-4-pentylbicyclo[2,2,2]-octane-1-carboxylic acid, Mallinckrodt MP-2269, Vancouver SMRM, April 1997; 4-[hydroxymethyl-(4,4-diphenyl)cyclohexyloxy-phosphoric acid diester]-3,6,9-carboxymethyl-3,6,9-triazaundecane-1, 11-dicarboxylic acid (MS-325), WO 96/23526; 4-[hydroxymethyl-(10-phenyl)-decyloxy-phosphoric acid diester]-3,6,9-carboxymethyl-3,6,9-triazaundecane-1,11-dicarboxylic acid (MS-323, WO 96/23526); N-(4-Decylphenylcarbamoylmethyl)-diethylenetriamine-N,N',N'',N''-tetracetic acid, EP 603403; 4,5-Diethyl-10,23-dimethyl-9,24-bis(3-hydroxypropyl)-16,17-bis[2-[2-(2-methoxyethoxy] ethoxy]-13,20,25,26,27-pentaazapentacyclo [20.2.1.]3,6.18, 11.0 14,19]heptacosa-3,5,8,10,12,14,16,18,20,22,24-undecane. U.S. Pat. No. 5,583,220 metal-chelating ligands that are chelated to a radioisotope selected from the group consisting of 153Samarium, 156Holmium, 165Dysprosium, 203Lead, 186Rhnenium, 188Rhenium, 88Yttrium, 90Yttrium, 211Bismuth 212Bismuth, 213Bismuth, and 214Bismuth.

Despite encouraging preclinical and clinical outcomes with RFA, PDT and VTAs to induce therapeutic tumor necrosis, viable tumor residuals are frequently attributed to the eventual incomplete therapy and tumor relapse [Pass H, JNatl Cancer Inst 1993; 85: 443-56; Thorpe P E. Clin Cancer Res. 2004; 10: 415-27., Skliarenko J V, et al. Cancer Res. 2006; 66: 2074-80].

For instance with VTAs, the local nonresponsiveness to the therapy is mainly due to the fact that peripheral tumor tissue is nourished by the blood from the surrounding normal vessels that are not targeted by VTAs, which represents a major hurdle for many pharmaceutical companies to commercialize their own VTA products. A typical example of tumor marginal escape from being attacked is illustrated in FIG. 11. In view of the striking target-to-nontarget ratio as high as 60-80 as quantified by autoradiography, therapeutically radionuclide labeled NACCs, which are non immune-originated and have a molecular weight smaller than 5 kDa, including napthodianthrone or phenanthro[1,10,9,8-opqra]perylene-7, 14-dione compounds, have been formulated as a therapy to improve the efficacy of necrosis-inducing cancer therapies such as RFA, PDT and VTAs. This results in improved tumor control and higher curability from the combination of a primary attack to cause bulky tumor necrosis and a secondary targeted radionuclide irradiation through administration of a therapeutically radionuclide labeled small NACC molecules to eliminate any residual viable tumor cells (FIG. 12).

A preferred treatment is a single dose VTA (e.g. CA-4P at 5-10 mg/kg) or a single treatment with RFA combined with a single or a serial for instance a double and or triple dose of MONO-[$^{131}$I]IODOHYPERICIN or $^{131}$I-MIH with an interval of 1 week using hypericin labeled with $^{131}$I-MIH or pamoate labeled with another radionuclide such as yttrium-90, rhenium-186 and rhenium-188. A murine model of liver tumor has been developed with intrahepatic implantation of radiation-induced fibrosarcoma (RIF-1) to mimic hepatic metastasis as the subject for experimental therapies. This model has been applied to demonstrate the benefit of VTAs, RFA tumoricidal activity of caused massive tumor necrosis and the successful antitumoricidal treatment with $^{131}$I-MIH in tumors with induced necrosis. This combined method of treatment is particularly suitable to prevent tumor relapse and the block the induced proliferation of residual viable tumor cells as a response of tumor tissue damage or ablation.

An advantage of the present invention is that utilizing the spectacular avidity of the therapeutically labeled NACC small molecules to the prior induced therapeutic tumor necrosis, the residual tumor tissues can be irradiated in close vicinity with therapeutic doses of radiation carried by therapeutically labeled NACC small molecules. NACCs such as hypericin are synthesized and labeled with a radiotherapeutic nuclide such as iodine-131 to produce a therapeutically radiolabeled NACC small molecule as exemplified by 131I-monoiodohypericin (131I-MIH) in FIG. 1H. Tumor necrosis has been targeted by intravenously administered phenanthro [1,10,9,8-opqra]perylene-7,14-dione derivatives labeled with iodine-131, e.g. 131I-MIH or 90Y-pamoate at a radiation dose of 3.5 MBq/mouse or higher. A preferred treatment for human patient is a radiation dose of 5 000 MBq-60 000 MBq and preferably 5 000 MBq-60 000 MBq, which depends on the body weight and therapeutic efficacy. The required radiation dose can also be estimated by a previous diagnostic measurement with diagnostically labeled NACC small molecules such as 123I-MIH and 99mTc-pamoate (another NACC). Preferably such diagnostic NACCs have the same strong affinity for necrosis and/or have chemical similarities for a correct calculation of the required therapeutic dose. For instance 123I-MIH is first used in a diagnostic measurement to estate the required therapeutic radiation dose for a therapeutic treatment by 131I-monoiodohypericin, or 99mTc-pamoate is used first in a diagnostic treatment to estimate the required therapeutic radiation dose in a therapeutic treatment with 90Y-pamoate. Other NACC molecules such as Photofrin II and ECIV-7, and the radionuclides other than iodine-131 and yttrium-90 such as rhenium-186 and rhenium-188 can be used for a combined treatment of a tumoricidal necrosis-inducing treatment together or in sequence with a therapeutically labeled NACC small molecules. Such Photofrin II or ECIV-7 can also be labeled with a diagnostic radionucleotide to firstly calculate the required therapeutic radiation dose and consequently use the therapeutically labeled Photophrin II or ECIV-7 in a combined (together or in sequence) treatment with tumoricidal compound to prevent tumor relapse and to block the proliferation reaction of viable tumor cells as a response to tumor damage, tumor ablation or tumor destruction. For instance the dosimetry over tumor tissue, for instance liver tumor, and other normal organs can be calculated using sequential gamma-camera or μ-SPECT measurements of iodine-123 labeled NACC small molecules to compare radiation absorption as cGy in the tumor versus normal organs and tissues.

A possible treatment to induce tumor necrosis is a single dose VTA (CA-4P at 5-10 mg/kg) alone, which can be combined with a single dose of 131I-MIH with an interval of 24 h to prevent tumor re-growth; or followed for one week by one or two repeated doses of 131I-MIH to compare tumor growth, animal survival or potential tumor cure in each condition. Another possible treatment is to complement RFA in an interval of 24 h with a single dose or repeated doses of 131I-MIH to prevent tumor relapse. 131I-MIH can be replaced by other therapeutically labeled NACCs.

REFERENCES TO THE GRAPHS IN THIS APPLICATION

perylene-7,14-diones derivatives consisting of hypericin (FIG. 1B), pseudohypericin (FIG. 1C), stentorin (FIG. 1D), the fringelites (FIG. 1E), the gymnochromes (Gymnochrome B (FIG. 1F), Gymnochrome D (FIG. 1G), Isogymnochrome D) and blepharismin (P. S. Song, 1995, J Photoscience 2, 21-35. A preferred therapeutically labeled phenanthro[1,10,9,8-opqra]perylene-7,14-dione derivatives is the compound with the structure as displayed in FIG. 1H.

FIG. 2 Treatment of liver rhabdomyosarcoma (R1) in rats with intravenous injection of a VTA combretastatin or CA-4P at a dose of 5 mg/kg. Before VTA therapy, contrast enhanced MRI reveals a hypervascular and hyperenhanced R1 tumor (arrow) in the liver (A). Dramatic vascular shutdown in R1 tumor a couple of hours after therapy is demonstrated as a hypointense and nonenhanced mass (arrow) on contrast enhanced MRI, suggesting tumoricidal effect of VTA (B). Two days after VTA therapy, the treated R1 tumor remains hypointense and unenhanced (arrow), suggestive of massive central necrosis. However, a strong rim enhancement appears at the periphery (C). Macroscopy proves this bulky necrotic tumor (arrow) with only a marginal rim showing fish-flesh like viable tumor tissue (D). The rectangular frame over the transition zone in C and D indicates where microscopy is focused. Photomicrograph (E) confirms the resultant central bulky necrosis (N), peripheral tumor regrowth (T) due to incomplete therapy, and neovasculature derived from normal liver (L) and labeled by greenish barium sulphate particles. Thus, the sub-millimeter zone of viable tumor in close vicinity of the necrosis offers an ideal condition for the present adjuvant anti-cancer therapy by combined use of small molecule therapeutically labeled NACCs.

FIG. 3 demonstrates the treatment of liver radiation-induced fibrosarcoma (RIF-1) in mice with radiofrequency ablation (RFA) 24 hours before iv injection of a NACC, i.e. hypericin (of fluorescent nature) at 5 mg/kg and 4 days before sacrifice. A: Tungsten-light macroscopy reveals a pale RFA lesion (arrow) encompassing necrotic RIF-1 tumor (NT) and necrotic liver (NL), the fish-flesh like viable tumor (VT) spared from RFA by intention, and adjacent untreated viable liver (VL). B: Corresponding UV light fluoromacroscopy demonstrates that 3 d after injection, hypericin is almost completely cleared from viable liver (VL) and viable tumor (VT), but is retained only in necrotic tumor (NT) and necrotic liver (NL), suggesting necrotropic property of this compound (arrow). The rectangular frame in A and B indicates where micrographs (C and D) were approximately focused. C: 3 d after injection, the fluorescent hypericin can still be detected in RFA-induced necrotic tumor regions (NT), particularly in close vicinity of the viable tumor (VT) as proven by the co-localized H&E stained histopathologic view (D). Thus, the prolonged retention of hypericin in necrosis matches well the radiation half life of iodine-131 (8 d) or yttrium-90 (64 h), which offers an ideal condition for the present adjuvant anti-cancer radiotherapy with combined use of a small molecule therapeutically labeled NACCs featuring multi-millimeter irradiation penetration (max. range of beta particles in tissue is 2.4 mm for iodine-131 and 12 mm for yttrium-90).

Treated mouse (ZD2661 50 mg/kg iv plus iodine-131-Hypericin 1.0 mCi iv): A: Before treatment, the tumor measures 19×11×7 mm³ in size; B: Twelve days after combined treatment, the tumor measures 17×10×5 mm³ in size; C: excised tumor specimen.

Control mouse (normal saline iv plus iodine-131-Hypericin 1.0 mCi iv): A': Before treatment, the tumor measures 16×9×5 mm³ in size; B': Twelve days after treatment of iodine-131-Hypericin alone, the tumor measures 20×10×8 mm³ in size; C': excised tumor specimen.

Notice that the tumor was larger before treatment but smaller after treatment in the mouse with dual treatments than that in the control mouse respectively.

The invention claimed is:

1. A therapeutically labeled napthodianthrone or phenanthro[1,10,9,8-opqra]perylene-7,14-dione compound, whereby the molecular weight of said compound is less than 2000 dalton, and whereby the therapeutic label is a radionuclide that has an unstable nucleus and emits radiation during its decay to a stable form, sufficient to locoregionally destroy neighboring cells or tissues, for use in a method of treating cancer in a warm-blooded animal in combination with a necrosis-inducing antitumor therapy, wherein the therapeutic label is selected from the group consisting of:
$^{88}$Yttrium, $^{90}$Yttrium, $^{91}$Yttrium, $^{89}$Yttrium, and $^{131}$Iodine.

2. The therapeutically labeled napthodianthrone or phenanthro[1,10,9,8-opqra]perylene-7,14-dione compound according to claim 1, which is selected from the group consisting of hypericin, pseudohypericin, stentorin, a fringelite, Gymnochrome B, Gymnochrome D, Isogymnochrome D and blepharismin.

3. The therapeutically labeled napthodianthrone or phenanthro[1,10,9,8-opqra]perylene-7,14-dione compound according to claim 1, whereby said compound is iodine-131-hypericin.

4. The therapeutically labeled napthodianthrone or phenanthro[1,10,9,8-opqra]perylene-7,14-dione compound according to claim 1, whereby the therapeutic label is in amount to obtain a radiation dose of 25-350 MBq/kg.

5. The therapeutically labeled napthodianthrone or phenanthro[1,10,9,8-opqra]perylene-7,14-dione compound according to claim 1, for use in a combined (together or in sequence) treatment with a drug selected from the group consisting of a vascular targeting agent, a pyruvate dehydrogenase kinase inhibitor such as AZD7545, dichloroacetate (DCA), sodium dichloroacetate, a halogenated acetophenone inhibitor, a radicicol oxime and radicicol.

6. The therapeutically labeled napthodianthrone or phenanthro[1,10,9,8-opgra]perylene-7,14-dione compound according to claim 1, whereby the therapeutic label is a beta emitter and the beta energy of the beta-emitter is >0.1 MeV and the beta-emitter has a radionuclide half-life of more than 1 day.

7. The therapeutically labeled napthodianthrone or phenanthro[1,10,9,8-opgra]perylene-7,14-dione compound according to claim 1, said compound further comprises a radiosensitiser, such as a triiodobenzene moiety, a borane moiety or carborane moiety.

8. The therapeutically labeled napthodianthrone or phenanthro[1,10,9,8-opgra]perylene-7,14-dione compound according claim 1, whereby said compound has one or more dichloroacetate moieties.

9. A kit comprising:
(a) a drug of the group consisting of a tumoricidal compound, a chemotherapeutic agent, an anti-tumor agent and a vascular targeting agent, and
(b) a therapeutically labeled napthodianthrone or phenanthro[1,10,9,8-opgra]perylene-7,14 dione compound, whereby the molecular weight of said compound is less than 2000 dalton, said compound comprising a chemical element or an isotope that has an unstable nucleus and emits radiation during its decay to a stable form sufficient to locoregionally destroy neighboring cells or tissues wherein the therapeutic label is selected from the group consisting of:
$^{88}$Yttrium, $^{90}$Yttrium, $^{91}$Yttrium, $^{89}$Yttrium, and $^{131}$Iodine.

10. The kit according to claim 9, wherein the drug is selected from:
the vascular targeting agent, combretastatin or an analog thereof, or a pharmaceutically acceptable salt thereof,
the water-soluble phosphate prodrug of the tubulin-binding agent ZD6126 (N-acetylcolchinol), and
the phosphate prodrug salt of combretastatin A-4.

11. The kit according to claim 9, wherein the therapeutically labeled napthodianthrone or phenanthro[1,10,9,8-opqra]perylene-7,14-dione compound is a compound of the group consisting of hypericin, pseudohypericin, stentorin, a fringelite, Gymnochrome B, Gymnochrome D, Isogymnochrome D and blepharismin.

12. The kit according to claim 9, wherein the therapeutically labeled napthodianthrone or phenanthro[1,10,9,8-opqra]perylene-7,14-dione compound comprises a radiolabel to provide 25-350 MBq/kg in a treatment.

13. The kit according to claim 9, wherein the therapeutically labeled napthodianthrone or phenanthro[1,10,9,8-opqra]perylene-7,14-dione compound has a radiation dose of 5 000 MBq-60 000 MBq.

14. A kit according to claim 9, for use in a method of treating cancer in a combined treatment of inducing tumor necrosis.

15. A therapeutically labeled napthodianthrone or phenanthro[1,10,9,8 opqra]perylene-7,14-dione compound, whereby the molecular weight of said compound is less than 2000 dalton, whereby the therapeutic label is a radionuclide that has an unstable nucleus and emits radiation during its decay to a stable form, sufficient to locoregionally destroy neighboring cells or tissues, for use in a method of treating cancer in a warm-blooded animal in combination with a necrosis-inducing antitumor therapy, wherein the therapeutic label is selected from the group consisting of $^{88}$Yttrium, $^{90}$Yttrium, $^{91}$Yttrium, $^{89}$Yttrium and $^{131}$Iodine, and whereby the therapeutic label is in an amount to obtain a radiation dose of 25-350 MBq/kg.

\* \* \* \* \*

UNITED STATES PATENT AND TRADEMARK OFFICE
CERTIFICATE OF CORRECTION

PATENT NO. : 8,741,262 B2  
APPLICATION NO. : 12/744798  
DATED : June 3, 2014  
INVENTOR(S) : Yicheng Ni et al.

Page 1 of 1

It is certified that error appears in the above-identified patent and that said Letters Patent is hereby corrected as shown below:

In the Claims

Column 12, Line 45, replace "[1,10,9,8-opgra]" with --[1,10,9,8-opqra]--.

Line 51, replace "[1,10,9,8-opgra]" with --[1,10,9,8-opqra]--.

Line 56, replace "[1,10,9,8-opgra]" with --[1,10,9,8-opqra]--.

Line 64, replace "[1,10,9,8-opgra]" with --[1,10,9,8-opqra]--.

Signed and Sealed this  
Sixteenth Day of September, 2014

Michelle K. Lee  
*Deputy Director of the United States Patent and Trademark Office*